United States Patent [19]

Wear et al.

[11] Patent Number: 5,608,059
[45] Date of Patent: Mar. 4, 1997

[54] ION-SENSITIVE COMPOUNDS

[75] Inventors: Trevor J. Wear, South Harrow; Christopher P. Moore, Rayners Lane; Alistair J. Goulden, Harrow; Paul D. Beer, South Parks; Nicholas C. Fletcher, South Parks Road, all of England

[73] Assignee: Eastman Kodak Company, Rochester, N.Y.

[21] Appl. No.: 356,187

[22] PCT Filed: Apr. 18, 1994

[86] PCT No.: PCT/EP94/01191

§ 371 Date: Dec. 19, 1994

§ 102(e) Date: Dec. 19, 1994

[87] PCT Pub. No.: WO94/24123

PCT Pub. Date: Oct. 27, 1994

[30] Foreign Application Priority Data

Apr. 21, 1993 [GB] United Kingdom ............... 9308213
Mar. 5, 1994 [GB] United Kingdom ............... 9404251

[51] Int. Cl.$^6$ ............... C07D 213/50; C07D 213/30; C07D 225/00; C07D 241/46
[52] U.S. Cl. ............... 540/465; 540/471; 544/225; 544/347; 546/2; 546/10; 546/316
[58] Field of Search ............... 546/316, 2, 10; 540/465, 450, 471; 544/347, 225

[56] References Cited

PUBLICATIONS

ACS Symp. Ser. vol. 537, (1994) Calvert et al, pp. 210–219 "Top–Surface Imaging".

J. Med. Chem. vol. 31, No. 24, (1993) Hale et al, "Novel Inhibitors".

J. Am. Chem. Soc. vol. 115, No. 10, (1993) Belser et al, "Supramolecular Ru / and or Os Complexes".

Primary Examiner—C. Warren Ivy
Assistant Examiner—Raymond Covington
Attorney, Agent, or Firm—John R. Everett

[57] ABSTRACT

Ion-sensitive compounds have the formula $A^{2+}B^{2-}$ wherein A represents a cation capable of forming a receptor-substrate complex with an anion, and B represents one or more counter anions, the cation being an anion receptor of the formula

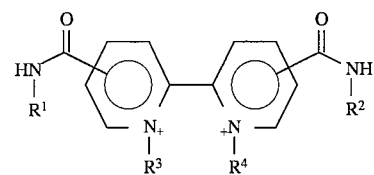

or

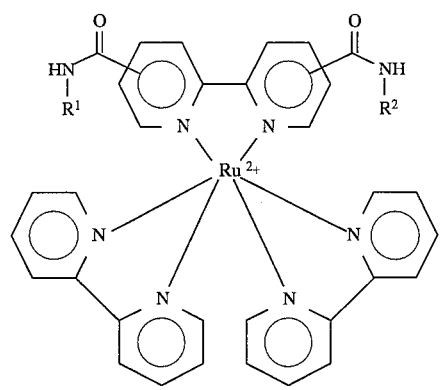

wherein $R^1$ and $R^2$ are each independently a substituted or unsubstituted alkyl group, a substituted or unsubstituted aryl group or $R^1$ and $R^2$ taken together with the atoms separating them represent the atoms necessary to complete a (2)-cryptand; and, $R^3$ and $R^4$ are each independently H or a lower alkyl group having from 1 to 4 carbon atoms, or $R^3$ and $R^4$ taken together represent an ethylene bridging group.

The compounds may be used for sensing anions.

5 Claims, 3 Drawing Sheets

ION-SENSITIVE COMPOUNDS

FIELD OF THE INVENTION

The invention relates to ion-sensitive compounds. More particularly, the invention relates to ion-sensitive compounds comprising a receptor designed to bind anionic species by the formation of a receptor-substrate complex.

BACKGROUND OF THE INVENTION

Anion receptors comprising a plurality of quaternary amine groups are known. Examples of such compounds may be seen in P.G. Potvin and J-M Lehn, *Prog. Macrocyclic Chem.*, 1987, 3, 214.

L.A. Summers, "The Bipyridinium Herbicides", Academic Press, New York, 1980, describes the use of certain compounds comprising diquaternary 2,2'-bipyridinium moieties in herbicidal applications.

Metal ion centres have also been utilised in systems for the recognition of anions as described in D.N. Reinhoudt, *J. Am. Chem. Soc.* 1992, 114, 9671–9673.

PROBLEM TO BE SOLVED BY THE INVENTION

There is a continuing need to provide new receptor compounds for a variety of applications. For example, there is a need for compounds which can be incorporated in electrochemical or optical sensors for anion determination. There is also a need for compounds which can be used in removal devices where levels of a given anion need to be kept low.

It is also desirable to provide receptor compounds which can be readily synthesised.

SUMMARY OF THE INVENTION

The ion-sensitive compounds of the invention have the formula $A^{2+}B^{2-}$ wherein A represents a cation capable of forming a receptor-substrate complex with an anion, and B represents one or more counter anions, characterised in that the cation is an anion receptor represented by the formula I

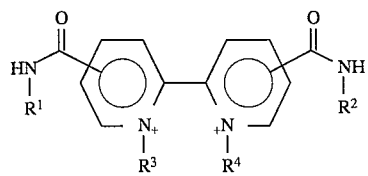

or by the formula II

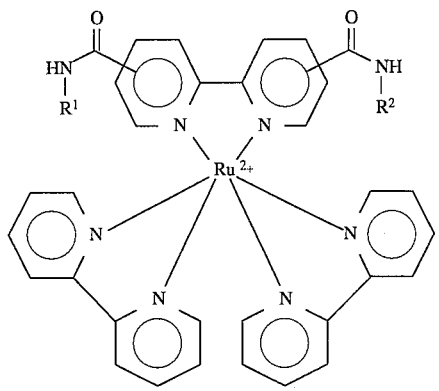

wherein $R^1$ and $R^2$ are each independently a substituted or unsubstituted alkyl group, a substituted or unsubstituted aryl group or $R^1$ and $R^2$ taken together with the atoms separating them represent the atoms necessary to complete a (2)-cryptand; and, $R^3$ and $R^4$ are each independently H or a lower alkyl group having from 1 to 4 carbon atoms, or $R^3$ and $R^4$ taken together represent an ethylene bridging group.

The invention also provides a method of sensing an anion in solution by contacting the anion with a compound comprising a cation which is a receptor for the anion to form a receptor-substrate complex and sensing a detectable change which results from the formation of the complex characterised in that the compound is a compound of the invention.

ADVANTAGEOUS EFFECT OF THE INVENTION

The compounds of the invention show selectivity to anions and are useful for the electrochemical and/or optical detection of anions, especially halides and particularly chlorides.

DETAILED DESCRIPTION OF THE INVENTION

Figure 1:
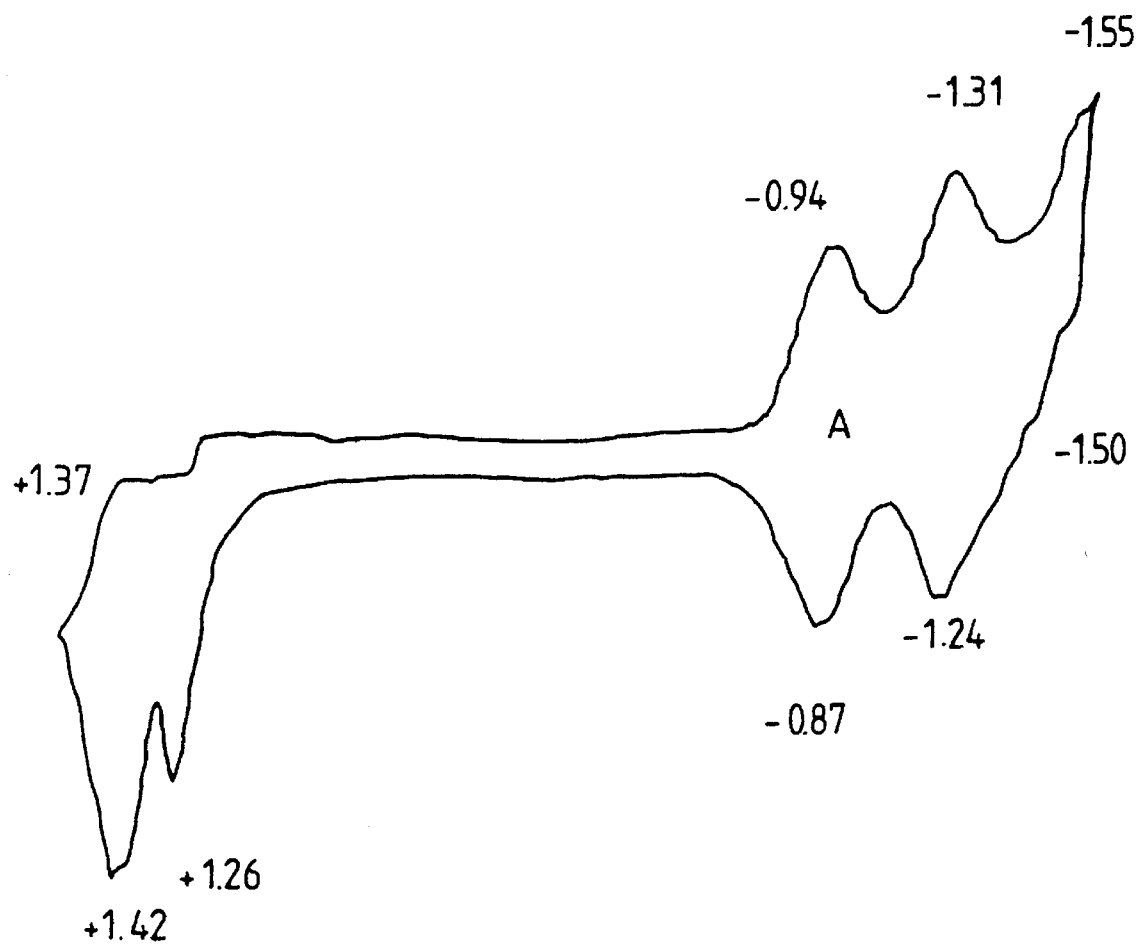
FIG. 1 is a cyclic voltammogram of a compound of the invention.

Preferably, $R^1$ and $R^2$ are each independently a substituted or unsubstituted alkyl group having from 1 to 20 carbon atoms e.g. methyl, ethyl, propyl, butyl, pentyl, hexyl, eicosyl. Suitable substituents include alkyloxy, aryloxy, alkylamido, arylamido, atkylsulfonamido, arylsulfonamido, dialkylamino, cyano and nitro. Specific examples of such $R^1$ and $R^2$ groups include butyl and methoxyethyl.

Preferably, $R^1$ and $R^2$ are each independently a substituted or unsubstituted phenyl group. Suitable substituents include alkyloxy, aryloxy, alkylamido, arylamido, alkylsulfonamido, arylsulfonamido, dialkylamino, cyano and nitro. A specific example of such a group is 3,4-dimethoxyphenyl.

R¹ and R² taken together with the atoms separating them may represent the atoms necessary to complete a (2)-cryptand. Preferably, the (2)-cryptand comprises two ionisable hydroxy groups. The two ionisable hydroxy groups together with the two amide protons shown in formula I and II are preferably arranged tetrahedrally with respect to each other within the cavity defined by the (2)-cryptand. Preferably, the (2)-cryptand comprises a bridged, conformationally locked ring system. In a particularly preferred embodiment, the (2)-cryptand comprises a bridged calix(4)arene. Attachment of the calix(4)arene to the two amide groups shown in formula I and II may be through the 1 and 3 positions of the calix(4)arene, respectively, whereby the 2- and 4-hydroxy groups in the calix(4)arene ring represent two ionisable hydroxy groups.

Preferably, R¹ and R² taken together have the following structure

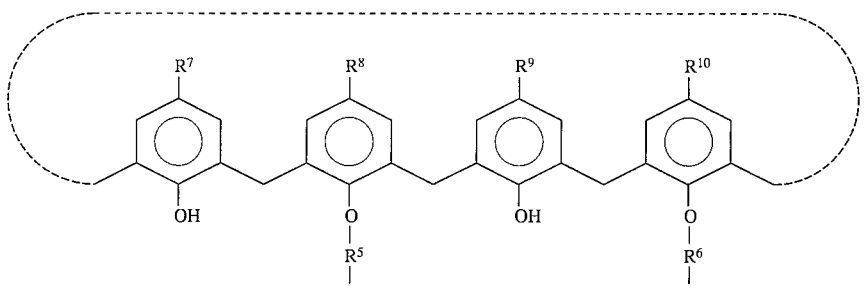

wherein
$R^7$, $R^8$, $R^9$ and $R^{10}$ are each independently hydrogen, a substituted or unsubstituted alkyl group, a substituted or unsubstituted aryl group, an alkylamido group, an arylamido group, an alkylsulfonamido group, an arylsulfonamido group or a nitro group; and,
$R^5$ and $R^6$ are each independently a substituted or unsubstituted alkylene group e.g. —$(CH_2)_2$—.

Preferably, $R^7$, $R^8$, $R^9$ and $R^{10}$ are each independently H, a substituted or unsubstituted alkyl group having from 1 to 20 carbon atoms e.g. methyl, ethyl, propyl, butyl, pentyl, hexyl and eicosyl. Tertiary alkyl groups are particularly preferred e.g. t-butyl. Suitable substituents include alkylamido, arylamido, alkoxycarbonyl, aryloxycarbonyl, alkylsulfonamido, arylsulfonamido, alkylcarbonyl, alkoxy, cyano and nitro.

Preferably, $R^7$, $R^8$, $R^9$ and $R^{10}$ are each independently a substituted or unsubstituted phenyl group. Suitable substituents include alkyloxy, aryloxy, alkylamido, arylamido, alkylsulfonamido, arylsulfonamido, alkyloxycarbonyl, aryloxycarbonyl and nitro.

Preferably, $R^3$ and $R^4$ are each methyl groups.

$B^{2-}$ represents any suitable anions which together with $A^{2+}$ are capable of forming a stable compound. Examples of such anions include sulphate, nitrate, phosphate, borate and halide e.g. iodide. Preferably, $B^{2-}$ represents weakly coordinating anions such as hexafluorophosphate and tetrafluoroborate.

The 4,4'- and 5,5'-amide disubstituted bipyridine compounds of the invention can be synthesised via condensation reactions of respective 4,4'- and 5,5'-bischlorocarbonyl-2,2,'-bipyridines with appropriate primary amines e.g. an arylamine, an alkylamine or a bisaminecalix(4)arene. The resulting bisamide can then be quaternised to give compounds of structure I e.g. by sequential treatment with dialkyl sulphate and ammonium hexafluorophosphate. Alternatively, the resulting bisamide can be converted into a compound of structure II by reaction with [RuCl₂(bipy)₂].2H₂O e.g. by refluxing with [RuCl₂(bipy)₂].2H₂O in a suitable solvent such as ethylene glycol. The resulting complex can be precipitated on addition of a suitable salt such as ammonium hexafluorophosphate.

The compounds of the invention can be used in a method of sensing anions, as indicated above. The detectable change resulting from formation of the complex can be measured by any suitable means such as NMR measurement, electrochemical measurement e.g. cyclic voltammetry, or optical measurement e.g. fluorescence spectroscopy.

Specific examples of the preparation of compounds of the invention are given as follows.

EXAMPLE 1

N,N'Dibutyl-6,6'-binicotinamide 5,5'dicarboxy-2,2'bipyridine (0.24 g, 0.98 mmol) was refluxed in 25 ml of thionyl chloride freshly distilled from triphenylphosphite for 40 hours under nitrogen. The solid eventually disappeared to produce a yellow solution, after which the excess thionyl chloride was distilled off and the yellow solid was dried for several hours in vacuo. The 2,2'-bipyridyl-5,5'-dicarboxylic acid chloride was dissolved in dry THF (20 ml) to which was then added dropwise butylamine (10 ml, 101 mmol) dropwise at room temperature under nitrogen and washed in 10 ml THF. A white precipitate formed almost immediately. The reaction was then stirred for 24 hours after which the solid was removed by filtration and washed with THF 3×20 ml and water 2×10 ml. The solid was then heated in 50 ml deionised water at 90° C. for 30 minutes after which it was filtered and dried in the oven (0.20 g, 57%).

Elemental analysis calculated for $C_{20}H_{26}N_4O_2$; C, 67.8%, H, 7.4%, N, 15.8%. Found C, 66.6%, H, 7.7%, 15.6%.

5,5'-Di(butylaminooxo)-1,1'-dimethyl-2,2'-bipyridinium dihexafluorophosphate 5,5'-Di(butylaminooxo)-2.2'-bipyridine (0.11 g, 0.31 mmol) was heated at 80° C. in dimethylsulphate (10 ml, 106 mmol) for 24 hours to produce a red solution. The dimethylsulphate was distilled off under reduced pressure. The solid was dissolved in 100 ml deionised water to which was added ammonium hexafluorophosphate (2.00 g, 12 mmol) in 5 ml water which gave a brown precipitate, which was collected by vacuum filtration. The brown precipitate was purified by column chromatography on silica with acetonitrile as the elutant giving a brown solid after removal of the solvent (0.12 g, 57%).

The compound has the structure of Formula I wherein $R^1$ and $R^2$ are each butyl and $R^3$ and $R^4$ are each methyl.

EXAMPLE 2

2,2'-Bipyridyl-5,5'-dicarboxylic acid 5,5'Dimethyl-2,2'-bipyridine (4.53 g, 24.6 mmol) was dissolved in concentrated sulphuric acid (50 ml). After cooling to 0° C. chromium (VI) oxide (14.88 g, 148.8 mmol) was ground and added in small proportions over a 2 hour period. The red mixture was heated to 65° C. for 17 hours while stirring giving a green solid which was washed into 350 ml ice/water with concentrated sulphuric acid (50 ml) to give a fine green suspension. The green solid was isolated over several days via vacuum filtration. The solid was dissolved up in 4M sodium hydroxide (500 ml) which was then acidified with 1M hydrochloric acid to pH8 whereupon chromium (III) hydroxide precipitated. The dark green precipitate was filtered off under gravity to give a pale yellow filtrate which upon further acidification with 1M hydrochloric acid to pH1 precipitated the product which was collected by vacuum filtration and dried in vacuo (yield 4.89 g, 81%).

N,N'-Bi(3,4-dimethoxyphenyl)-6.6'-binicotinamide 5,5'-dicarboxy-2,2'-bipyridine (0.50 g, 2.05 mmol) was refluxed in 25 ml of thionyl chloride freshly distilled from triphenylphosphite for 22 hours under nitrogen. The solid eventually disappeared to produce a yellow solution, after which the excess thionyl chloride was distilled off and the yellow solid was dried for several hours in vacuo. The 2,2'-bipyridyl-5,5'-dicarboxylic acid chloride .was then used in situ without further isolation. The yellow solid was partly dissolved up in dry THF (10 ml) to which was then added dropwise 4-aminoveratrole (6.31 g, 41.1 mmol) dropwise in dry THF (30 ml) at room temperature under nitrogen and washed in with a further 10 ml THF. A buff precipitate formed almost immediately. The reaction was then stirred for 15 hours after which the solid was removed by filtration and washed with THF 3×20 ml and water 2×10 ml. The solid was then heated in 50 ml deionised water at 90° C. for 30 minutes after which it was filtered and dried in the oven (0.42 g, 47%) .

The compound has the structure of Formula II wherein $R^1$ and $R^2$ are each 3,4-dimethoxyphenyl.
Elemental analysis calculated for $C_{28}H_{26}N_4O_6$;C, 65.4%, H, 5.1%, N, 10.9%. Found C, 64.1%, H, 5.1%, 10.4%.

$Ru^{(II)}$(bipyridyl)$_2$ Complex Salt 5,5'-Bis(3,4-dimethoxyphenylaminooxo )-2,2'-bipyridine (0.10 g, 0.195 mmol) was dissolved in DMF (40 ml) with $[Ru^{(II)}(bipy)_2Cl_2].2H_2O$(0.103 g, 0.195 mmol) and heated at 80° C. for 17 hours. The solution went from purple to dark brown, the solution was filtered, and washed with 10 ml water. The volume was reduced, and ammonium hexafluorophosphate (2.5 g, 15 mmol) in 5 ml of water was added. A brown precipitate was obtained, which was purified on Sephadex LH20 in acetonitrile methanol 50:50.
Elemental analysis calculated for $C_{48}H_{42}N_8O_6RuP_2F_{12}.H_2O$;C, 46.7%;H, 3.6%;N, 9.1%. Found C, 46.2%; H, 3.5%; N, 9.1%.

EXAMPLE 3

1,3 Biscyanocalix(4)arene

A slurry of paratertiarybutylcalix(4)arene (3.0 g, 4.05 mmol) and anhydrous potassium carbonate (1.12 g, 8.1 mmol) was stirred in predried acetone (100 ml) at room temperature for 10 minutes. Bromoacetonitrile (0.77 ml, 8.1 mmol)was added and the reactants stirred for 48 hours at room temperature. The salt precipitated was removed by filtration and the acetone removed under reduced pressure to leave the crude product. This was taken up in dichloromethane and washed with 1×100 ml hydrochloric acid, the solvent again removed under reduced pressureto leave the product as a white crystalline solid. Yield 95%.

1,3 Bisaminecalix[4]arene

A slurry of the 1,3 biscyanocalix[4]arene (1.5 g, 2.2 mmol) and lithium aluminjure hydride (0.66 g, 17.6 mmol) was refluxed in dry diethylether (75 ml) for 4 hours under a nitrogen atmosphere. The reaction flask was then placed into an ice bath and the excess lithium aluminium hydride destroyed using water (dropwise, vigorous stirring). The alumina precipitated was filtered and washed with chloroform and the solvents removed under reduced pressure to leave the product as a white crystalline solid. Yield 75%.

Bipyridylcalix[4]arene

The 1,3 bisaminecalix[4]arene (1.00 g, 1.36 mmol), triethylamine (0.38 ml, 2.72 mmol) and dimethylaminopyridine (microspatulae) were dissolved in dichloromethane (250 ml) and stirred at room temperature under a nitrogen atmosphere. To this mixture 4,4'-bischlorocarbonyl-2,2'-bipyridine (0.34 g, 1.36 mmol) in dichloromethane (100 ml) was added dropwise. White fumes. of triethylamine hydrochloride were observed on the addition and the reactants were stirred for a further 16 hours at room temperature. The reaction mixture was washed with 3×100 ml water, dried over magnesium sulphate and the solvent removed under reduced pressure to leave the crude pink product. This was purified using column chromatography. Silica (mesh 230–400); eluent methanol:ethylacetate:dichloromethane (2:2:1), (Rf 0.80). Yield 35%.

On scaled-up reactions the amine and acid chloride were added simultaneously to a stirring solution of triethylamine and dimethylaminopyridine in dry dichloromethane. The crude product was first purified on a silica column using an eluent of chloroform:acetone:methanol.(6:2:1), (Rf 0.35) followed by a second column as stated above.

Bipyridyl Ruthenium Complex PF$_6$-Salt

A slurry of the bipyridylcalix[4]arene (0.10 g, 0.106 mmol) and ruthenium dipyridyl (0.055 g, 0.106 mmol) in ethanol (4 ml), water (4 ml) and acetic acid (0.5 ml) was refluxed for 4–6 hours. The reaction was followed using silica thin layer chromatography plates with an eluent the same as the reaction solvent. The product formation is monitored using long wavelength ultra violet light and appears at Rf 0.38. On completion of the reaction the solvents were removed under reduced pressure followed by further drying under high vacuum at 50° C. The crude reaction mixture was purified on a Sephadex™ column (LH20-100) eluent neat acetonitrile. The column was eluted very slowly and the orange product collected after approximately 5 hours. Fractions were monitored by thin layer chromatography as described above. The solvent was removed from the product under reduced pressure to leave the chloride salt of the complex. The chloride salt was taken up in water and deposited as the hexafluorophosphate salt by addition of ammonium hexafluorophosphate to the solution. Yield 65%.

The compound has the structure of Formula II wherein $R^1$ and $R^2$ taken together have the calix(4)arene structure described above in which $R^7$, $R^8$, $R^9$ and $R^{10}$ are each tert-butyl and $R^5$ and $R^6$ are each —(CH$_2$)$_2$—.

The chemical structures of the compounds prepared in Examples 1 to 3 were confirmed by NMR and mass spectroscopy measurements.

EXAMPLE 4

On addition of tetrabutyl ammonium chloride (TBAC) to a solution of the compound of Example 2 in deuteriochloroform a shift was observed in the $^1$H NMR signals due to protons adjacent to the chloride binding site. These results are shown below.

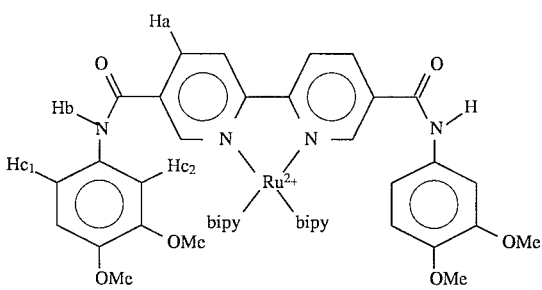

wherein bipy represents bipyridyl.

| Proton | Δδ/ppm<br>1 × Cl$^-$ | Δδ/ppm<br>2 × Cl$^-$ |
|---|---|---|
| a | 0.10 | — |
| b | 0.21 | 0.32 |
| c$_1$ | 0.07 | 0.11 |
| c$_2$ | 0.05 | 0.07 |

The cyclic voltammogram of the compound was recorded as shown in FIG. 1. This was very similar to that of known ruthenium (II) tris-bipyridyl complexes whose electrochemical response has been well documented.

The cathodic shifts observed on addition of chloride anion to the compound of Example 2 (peak A) are shown as follows:

| Equivalents of Cl | 1.0 | 2.0 | 5.0 |
|---|---|---|---|
| Oxidation Shift (V) | 0.01 | 0.02 | 0.03 |
| Reduction Shift (V) | 0.01 | 0.02 | 0.04 |

Figure 2:
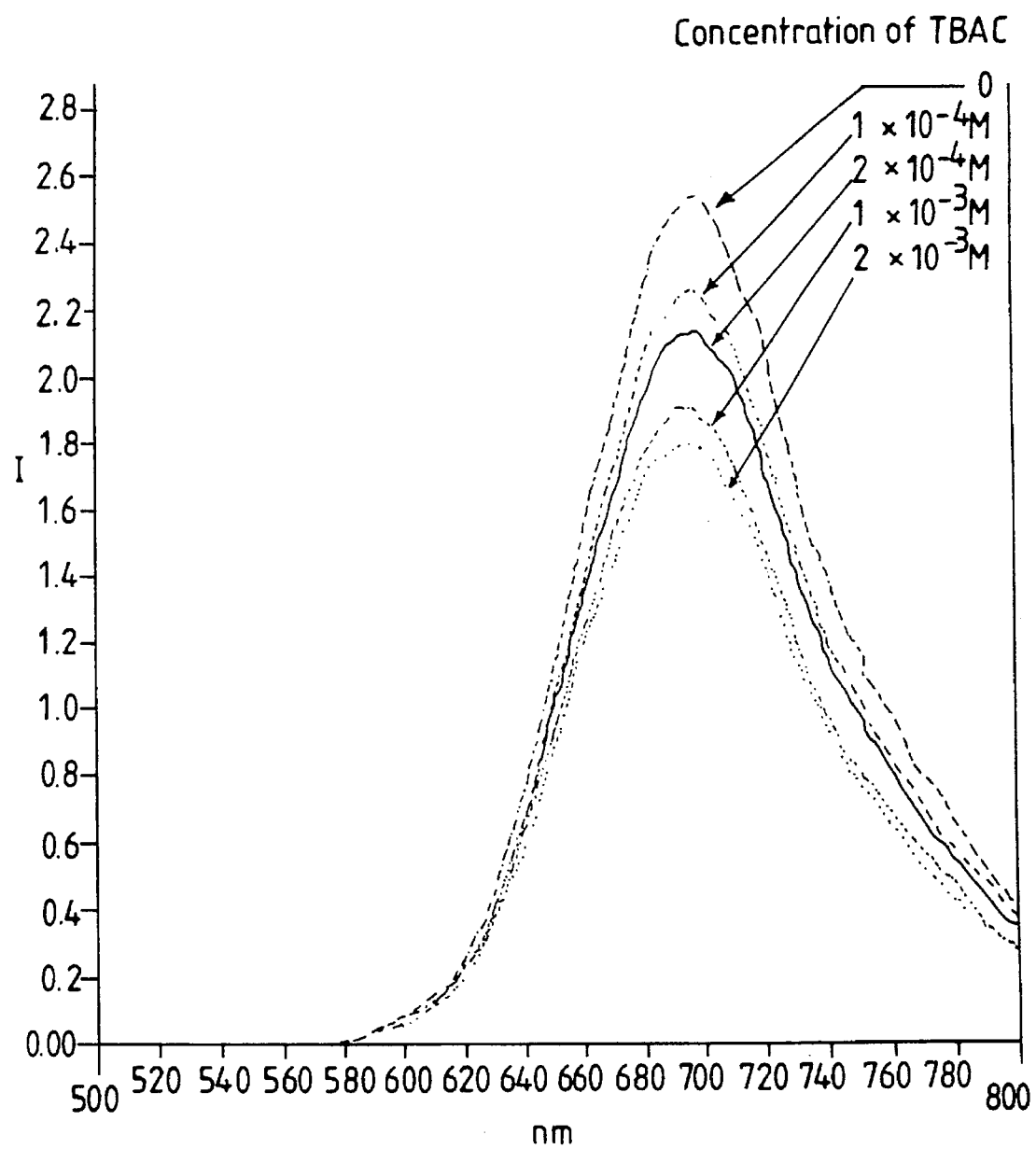
FIG. 2 is a graph showing the fluorescence of a compound of the invention.

The effect of the addition of chloride ions on the fluorescence of the compound of Example 2 is shown in FIG. 2. Increasing chloride concentration causes a decrease in fluorescence.

EXAMPLE 5

On addition of tetrabutyl ammonium chloride to the compound of Example 1 a downfield shift was observed in the $^1$H NMR signals due to protons adjacent to the chloride binding site. These results are shown below:

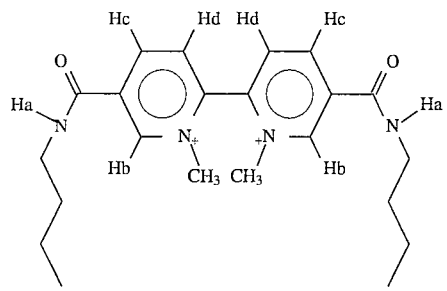

wherein the proton atoms of the methyl groups are the "e" protons.

| Proton | Δδ/ppm<br>+1 equivalent of Cl$^-$ | Δδ/ppm<br>+2 equivalent of Cl$^-$ |
|---|---|---|
| a | 0.29 | 0.54 |
| b | 0.19 | 0.27 |
| c | 0.12 | 0.17 |
| d | 0.05 | 0.07 |
| e | 0.02 | 0.02 |

EXAMPLE 6

Figure 3:
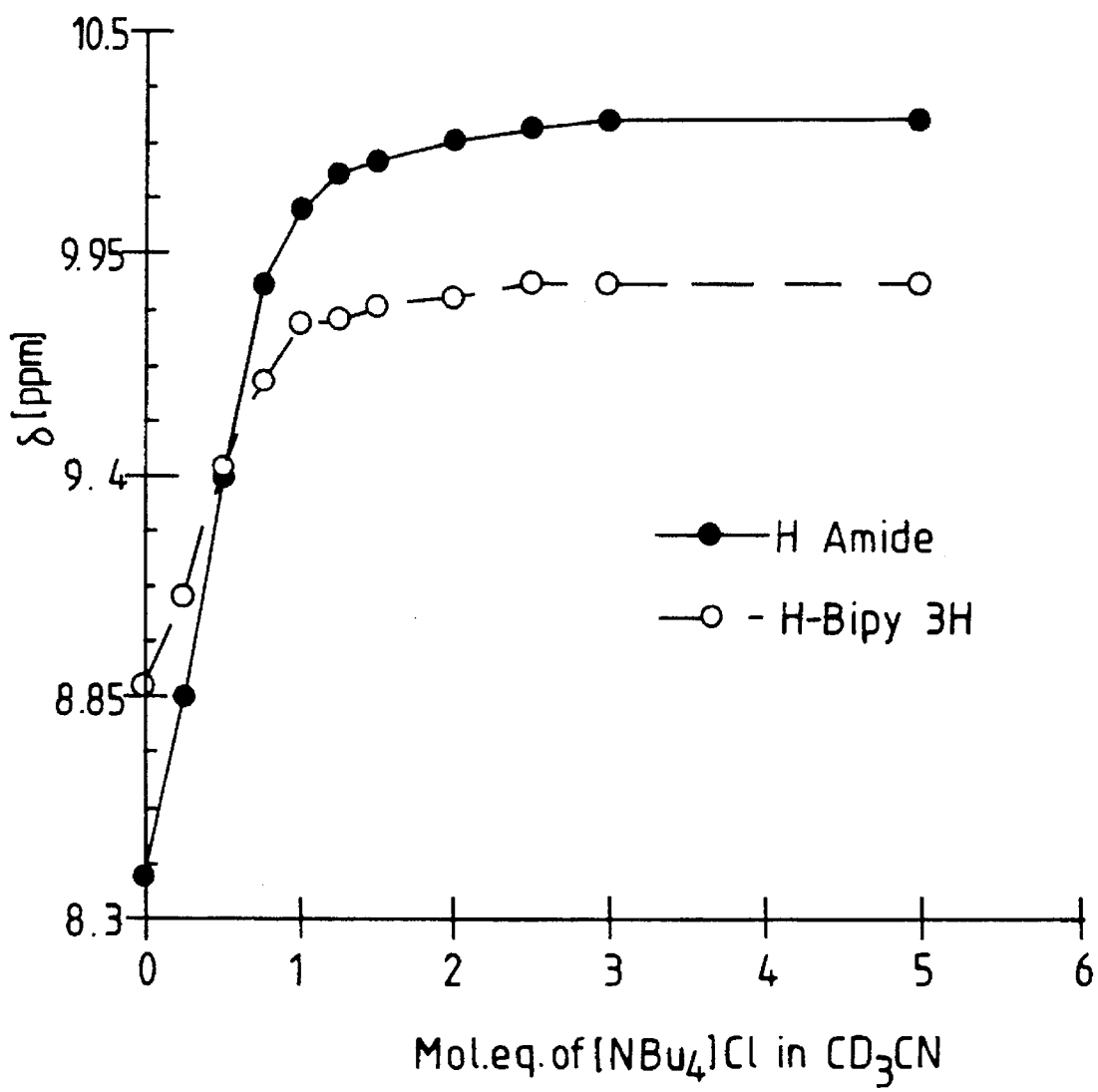
FIG. 3 is a $^1$H NMR titration curve of a compound of the invention and Cl⁻ in CD$_3$CN solution.

Anion recognition by the compound of Example 3 has been demonstrated by $^1$H NMR and cyclic voltammetry. Addition of tetrabutyl ammonium halides, hydrogen sulphate and dihydrogen phosphate to solutions of the compound in CD$_3$CN resulted in perturbations of the receptor's protons. With chloride, the amide proton of the compound is shifted downfield by Δδ1.5ppm; the 3,3'-bipyridyl proton of the receptor was also perturbed. These effects are summarised in the resulting titration curve shown in FIG. 3.

Comparison of the results of cyclic voltammetry for the compound of the invention shown in Table 1 below with the known electrochemical properties of [(bipy)₃Ru](PF₆)² provides further evidence for anion recognition.

| Redox couple | +3/+2[d] | +2/+1[e] | +1/0[e] | 0/−1[e] |
|---|---|---|---|---|
| $E_{1/2}$(free, V)[a] | 1.12 | −1.39 | −1.79 | −2.02 |
| $\Delta E(H_2PO_4^-$,mV)[b,c] | — | 175 | <5 | <5 |
| $\Delta E(HSO_4^-$,mV)[b] | — | 15 | <5 | <5 |
| $\Delta E(Cl^-$,mV)[b] | — | 70 | <5 | <5 |
| $\Delta E(Br^-$,mV)[b] | — | 60 | <5 | <5 |
| $\Delta E(I^-$,mV)[b] | — | 40 | <5 | <5 |

[a]Obtained in acetonitrile solution containing 0.1M [Bu$^n_4$N]PF₆ as supporting electrolyte. Solutions were about 5 × 10⁻⁴M in compound and potentials were determined with reference to a Ag⁺/Ag electrode (330 ± 5 mV vs. SCE) at 21 ± 1° C. at 50 mVs⁻¹ scan rate.
[b]Cathodic shifts of reduction potential produced by presence of anions (up to 10 equivalents) added as their tetrabutyl ammonium salts.
[c]DMSO was added (up to 50% v/v) before the addition of $H_2PO_4^-$ to prevent precipitation of complex.
[d]Metal centred oxidation.
[e]Ligand centred reduction.

We claim:

1. An ion-sensitive compound having the formula $A^{2+}B^{2-}$ wherein A represents a cation capable of forming a receptor-substrate complex with an anion, and B represents one or more counter anions, characterised in that the cation is an anion receptor represented by the formula

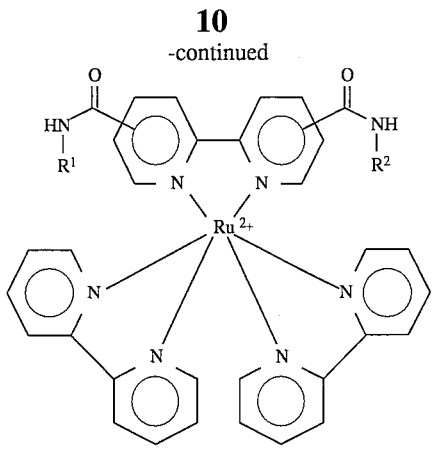

wherein
R¹ and R² are each independently a substituted or unsubstituted alkyl group, a substituted or unsubstituted aryl group or R¹ and R² taken together with the atoms separating them represent the atoms necessary to complete a (2)-cryptand; and,
R³ and R⁴ are each independently H or a lower alkyl group having from 1 to 4 carbon atoms, or R³ and R⁴ taken together represent an ethylene bridging group.

2. A compound according to claim 1 wherein R¹ and R² are each independently a substituted or unsubstituted alkyl group having from 1 to 20 carbon atoms.

3. A compound according to claim 1 wherein R¹ and R² are each independently a substituted or unsubstituted phenyl group.

4. A compound according to claim 1 wherein R¹ and R² taken together have the following structure

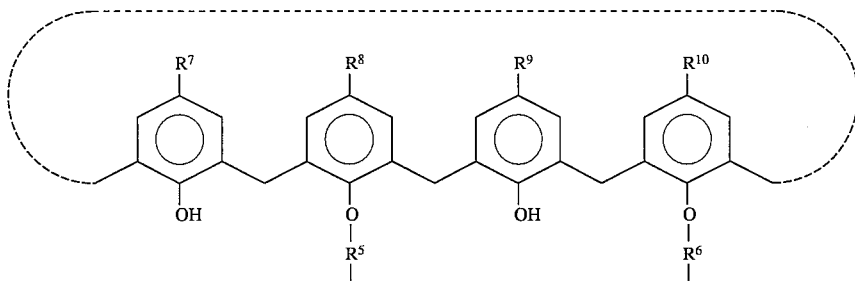

wherein
R⁷, R⁸, R⁹ and R¹⁰ are each independently hydrogen, a substituted or unsubstituted alkyl group, a substituted or unsubstituted aryl group, an alkylamido group, an arylamido group, an alkylsulfonamido group, an arylsulfonamido group or a nitro group; and, R⁵ and R⁶ are each independently a substituted or unsubstituted alkylene group.

5. A compound according to any one of the preceding claims wherein R³ and R⁴ are each methyl groups.

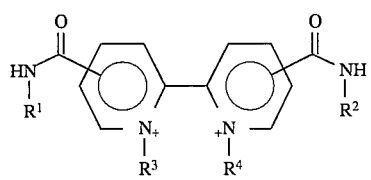

or

* * * * *